United States Patent [19]

Hartenstein et al.

[11] 4,425,350
[45] Jan. 10, 1984

[54] 5,6,6a,7-TETRAHYDRO-4H-DIBENZ(de,g)-ISOQUINOLINE DERIVATIVES, AND THEIR USE FOR TREATING CENTRAL NERVOUS SYSTEM DISORDERS

[75] Inventors: Johannes Hartenstein, Stegen-Wittental; Edgar Fritschi, St. Peter, both of Fed. Rep. of Germany

[73] Assignee: Warner-Lambert Company, Morris Plains, N.J.

[21] Appl. No.: 251,000

[22] Filed: Apr. 3, 1981

[30] Foreign Application Priority Data

Apr. 5, 1980 [DE] Fed. Rep. of Germany ....... 3013346

[51] Int. Cl.$^3$ .................. A61K 31/47; C07D 217/04; C07D 217/06
[52] U.S. Cl. .................. 424/258; 546/48; 546/75
[58] Field of Search .................. 546/48, 75; 424/258

[56] References Cited

U.S. PATENT DOCUMENTS 3,950,344  4/1976  Kupchan et al. .................. 546/75

OTHER PUBLICATIONS

Dyke et al., Tetrahedron, vol. 35, pp. 2555–2562 (1979).

Primary Examiner—Paul M. Coughlan, Jr.
Attorney, Agent, or Firm—Ronald a. Daignault

[57] ABSTRACT

The present invention provides compounds of the general formula:

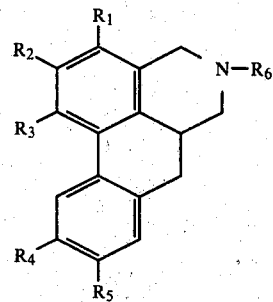

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is hydrogen, straight or branched-chain alkyl of from 1 to 5 carbon atoms, straight or branched-chain alkenyl of from 2 to 5 carbon atoms, cycloalkylalkyl of from 4 to 7 carbon atoms, alkoxy carbonyl of from 2 to 6 carbon atoms, trifluoroacetyl, aralkyl of from 5 to 11 carbon atoms, or acyl which is derived from an aliphatic, araliphatic or aromatic carboxylic acid of from 1 to 11 carbon atoms; and the pharmaceutically acceptable salts thereof; excluding 5,6,6a,7-tetrahydro-1-hydroxy-2,9,10trimethoxy-5-methyl-4H-dibenz(de,g)-isoquinoline and 5,6,6a,7-tetrahydro-1,2,9,10-tetramethoxy-5-methyl-4H-dibenz(de,g-)isoquinoline.

The present invention also provides a process for the preparation of these compounds and pharmaceutical compositions containing them. Furthermore, the present invention is concerned with the use of these compounds for treating diseases of the central nervous system.

19 Claims, No Drawings

5,6,6a,7-TETRAHYDRO-4H-DIBENZ(de,g)-ISOQUINOLINE DERIVATIVES, AND THEIR USE FOR TREATING CENTRAL NERVOUS SYSTEM DISORDERS

BACKGROUND OF THE INVENTION

The present invention is concerned with 5,6,6a,7-Tetrahydro-4H-dibenz(de,g)isoquinoline derivatives, with a process for their preparation, with pharmaceutical compositions containing them and with their use for combating diseases of the central nervous system.

Federal Republic of Germany Patent Specification No. 2,757,281 describes an oxidative ring closure reaction of 1-benzyl-7-hydroxy-1,2,3,4-tetrahydroisoquinoline derivatives by means of vanadium oxytrichloride which, without the introduction of a protective group on the nitrogen atom, proceeds smoothly and completely to give the 1-hydroxyaporphin system. An analogous reaction of 4-benzyltetrahydroisoquinoline with vanadium oxytrifluoride to give dibenz(de,g)isoquinoline is described in Tetrahedron, 35, 2555–2562/1979. This reference describes two compounds having similar structures to the compounds of the invention (reference compounds 9a and 9b), but these bases could only be isolated in 67% and 38% yields respectively from multicomponent mixtures. No utility for these compounds has previously been described.

Surprisingly, we have now found that the ring closure reaction of 4-benzyltetrahydroisoquinolines can give considerably purer products and correspondingly higher yields can be achieved when vanadium oxytrichloride is used instead of vanadium oxytrifluoride. This course of the reaction was not to have been expected since despite the modifications in the reaction described in the Tetrahedron article (loc. cit.), the reaction gave rise to black, tarry multicomponent mixtures when the synthesis of other bases was attempted. The authors were unable to find a generally useful, efficient means to prepare the dibenz(de,g)isoquinolines.

In addition to solving the synthetic problem, we have found that the dibenz(de,g)isoquinolines prepared according to the process of the present invention display valuable pharmacological properties and possess, in particular, a good neuroleptic action.

Therefore, they are especially useful for treating diseases of the central nervous system, for example, schizophrenia and Parkinson's disease, and endogenic depressions.

This discovery is also surprising since related 4-benzylisoquinolines (cf. Federal Republic of Germany Patent Specification No. 2,034,588, column 8, lines 54–57), which are typical spasmolytics, display a completely different activity profile and, even in the case of considerable dosages, do not exert any action on the central nervous system (see column 11, lines 9–15).

SUMMARY OF THE INVENTION

The Invention sought to be patented in its generic compound aspect is a compound having the structural formula I

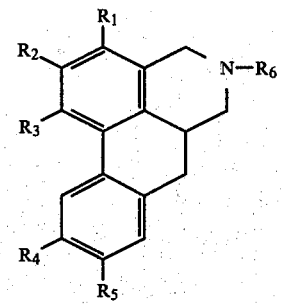

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is hydrogen, straight or branched-chain alkyl of from 1 to 5 carbon atoms, straight or branched-chain alkenyl of from 2 to 5 carbon atoms, cycloalkylalkyl of from 4 to 7 carbon atoms, alkoxy carbonyl of from 2 to 6 carbon atoms, trifluoroacetyl, aralkyl of from 5 to 11 carbon atoms, or acyl which is derived from an aliphatic, araliphatic or aromatic carboxylic acid of from 1 to 11 carbon atoms; and the pharmaceutically acceptable salts thereof; excluding 5,6,6a,7-tetrahydro-1-hydroxy-2,9,10-trimethoxy-5-methyl-4H-dibenz(de,g)isoquinoline and 5,6,6a,7-tetrahydro-1,2,9,10-tetramethoxy-5-methyl-4H-dibenz(de,g)isoquinoline.

The invention sought to be patented in a first subgeneric compound aspect is a compound having the structural formula I wherein $R_1$, $R_2$, $R_3$, $R_4$ and $R_5$ may be the same or different and are hydroxy, straight or branched-chain alkoxy groups of from 1 to 3 carbon atoms, phenoxy, benzyloxy, two adjacent groups may be methylenedioxy or hydrogen provided $R_4$ and $R_5$ are not simultaneously hydrogen; $R_6$ is hydrogen, straight or branched-chain alkyl of from 1 to 3 carbon atoms, straight or branched chain alkenyl of from 2 to 4 carbon atoms, cyclopropylmethyl cyclobeutylmethyl, cyclopentylmethyl, cyclohexylmethyl, alkoxycarbonyl of from 2 to 4 carbon atoms, benzyl, phenethyl, alkanoic acyl of from 1 to 5 carbon atoms, phenylalkanoic acyl of from 8 to 11 carbon atoms; and the pharmaceutically acceptable salts thereof; excluding 5,6,6a,7-tetrahydro-1-hydroxy-2,9,10-trimethoxy-5-methyl-4H-dibenz(de,g)isoquinoline and 1,2,9,10-tetramethoxy-5-methyl-4H-dibenz(de,g)isoquinoline.

The invention sought to be patented in a second subgeneric compound aspect is a compound having the structural formula I wherein $R_1$ and $R_3$ may be the same or different are hydrogen, hydroxy or methoxy; $R_2$ is methoxy, $R_4$ and $R_5$ may be the same or different and are hydroxy, methoxy or together form a methylenedioxy group, $R_6$ is hydrogen, methyl, or trifluoroacetyl; and the pharmaceutically acceptable salts thereof; excluding 5,6,6a,7-tetrahydro-1-hydroxy-2,9,10-trimethoxy-5-methyl-4H-dibenz(de,g)isoquinoline and 5,6,6a,7-tetrahydro-1,2,9,10-tetramethoxy-5-methyl-4H-dibenz(de,g)isoquinoline.

The invention sought to be patented in a generic process aspect is a process for preparing a compound having the formula

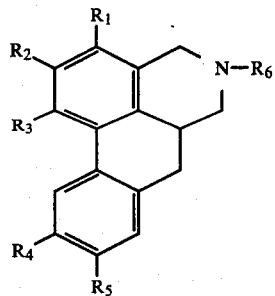

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is hydrogen, straight or branched-chain alkyl of from 1 to 5 carbon atoms, straight or branched-chain alkenyl of from 2 to 5 carbon atoms, cycloalkylalkyl of from 4 to 7 carbon atoms, alkoxy carbonyl of from 2 to 6 carbon atoms, trifluoroacetyl, aralkyl of from 5 to 11 carbon atoms, or acyl which is derived from an aliphatic, araliphatic or aromatic carboxylic acid of from 1 to 11 carbon atoms; and the pharmaceutically acceptable salts thereof; which comprises oxidising a compound of structural formula II

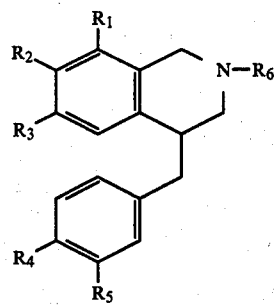

wherein $R_1$-$R_6$ are as defined above provided that at least one of $R_1$ and $R_3$ is hydroxyl, with at least one equivalent of vanadium oxytrichloride in the presence of a strong acid.

The invention sought to be patented in a generic pharmaceutical composition aspect is a composition useful for treating diseases of the central nervous system in a mammal consisting essentially of a compound having the structural formula I or mixtures thereof, in combination with a pharmaceutically acceptable carrier.

The invention sought to be patented in a pharmaceutical method aspect is a method for treating diseases of the central nervous system in a mammal in need of such treatment; which comprises administering an effective amount of the above defined pharmaceutical composition to said mammal.

DESCRIPTION OF THE PREFERRED EMBODIMENTS

For carrying out the process according to the present invention, the hydroxy-4-benzyl-1,2,3,4-tetrahydroisoquinoline derivatives of general formula (II) are dissolved in an organic solvent which is inert under the reaction conditions and, if $R_6$ is not to represent an acyl radical, mixed with at least one equivalent and preferably with an excess amount of vanadium oxytrichloride in the presence of at least one equivalent and preferably of an excess of a strong acid at a temperature of from ambient temperature to $-70°$ C. and preferably of $-5°$ to $-20°$ C.

Preferred examples of inert organic solvents which can be used include chlorinated hydrocarbons, especially methylene chloride, chloroform, dichloroethane and carbon tetrachloride.

Examples of acids which can be used include inorganic acids, such as hydrochloric acid, hydrobromic acid, perchloric acid, and strong organic acids such as trifluoroacetic acid, which can possibly also serve as solvents.

Vanadium oxytrichloride is preferably added to the solution of the tetrahydroisoquinoline in a mole ratio of from 1 to 3 and more preferably of 1.3 to 2.5 per mole of tetrahydroisoquinoline, optionally in a chemically inert solvent. A coloration of the reaction mixture to dark green-dark blue thereby takes place.

Thin layer chromatographic monitoring of the reaction shows that the oxidative cyclisation takes place practically quantitatively after about 5 to 45 minutes. In order to isolate the reaction products, the reaction mixture is evaporated in a vacuum and the residue partitioned between water and an organic solvent, optionally with rendering alkaline with ammonia, sodium carbonate or sodium bicarbonate.

The usual working up of the extract then gives the crude product which can be purified by crystallisation and/or chromatography. Working up can be carried out especially advantageously when using trifluoroacetic acid. In the case of this process variant, the reaction products of general formula (I), insofar as they have a basic nitrogen atom and $R_6$ is not to represent an acyl radical, can, as a rule, be isolated and purified directly as readily crystallising salts of trifluoroacetic acid in pure form. For this purpose, the reaction mixture, after stripping off the trifluoroacetic acid and possibly the solvent, is taken up in water and extracted with chloroform in which the trifluoroacetates are, surprisingly, readily soluble. The procedure permits an especially simple separation of the products from the vanadium salts, whereas under basic conditions the formation of precipitates of vanadium salts makes partitioning and isolation much more difficult.

The hydroxy-4-benzyltetrahydroisoquinolines of general formula (II) used as starting materials can be obtained from the 4-benzylisoquinolines described in the literature or in a manner analogous to that described in the literature (J. Org. Chem., 30, 2459/1965; Advances in Heterocyclic Chemistry, 14, 279 et seq./1979) by hydrogenation and/or reduction. Thus, for example, the 4-benzylisoquinolines can be converted into the methiodides and subsequently reduced with sodium borohydride to give tetrahydroisoquinolines.

The 4-benzyl-N-nortetrahydroisoquinolines can be obtained, for example, by the reduction of the 4-benzylisoquinolines in known manner with zinc/hydrochloric acid.

Since the hydroxy-4-benzyltetrahydroisoquinolines of general formula (II) serving as starting materials possess a chiral centre, they can be used either as enantiomers or as enantiomeric mixtures.

The bases obtained of general formula (I) are, for the purposes of purification or for galenical reasons, preferably converted into crystalline, pharmaceutically acceptable salts.

The salts can be obtained in the usual manner by neutralising the bases with appropriate inorganic or organic acids. Examples of acids which can be used include hydrochloric acid, sulphuric acid, phosphoric acid, hydrobromic acid, acetic acid, tartaric acid, lactic acid, citric acid, malic acid, salicylic acid, ascorbic acid, malonic acid, maleic acid or succinic acid, those of trifluoroacetic acid being preferred.

The alkyl, alkenyl and alkoxy group according to the present invention contain up to 5 and preferably up to 3 carbon atoms. The cycloalkylalkyl groups are preferably cycloalkylmethyl groups containing 4 to 7 carbon atoms, for example, cyclopropylmethyl, cyclobutylmethyl, and cyclopentylmethyl groups. The aralkyl groups are preferably phenylalkyl groups containing 7 to 10 carbon atoms such as benzyl and phenethyl groups. Aliphatic carboxylic acids are to be understood to be preferably monobasic acids containing up to 5 carbon atoms and araliphatic acids are preferably phenylalkane acids containing 8 to 11 carbon atoms.

One preferred group of compounds according to the present invention are those wherein $R_1$, $R_2$, $R_3$, $R_4$ and $R_5$, which can be the same or different, are hydroxyl groups, straight or branched-chain alkoxy radicals containing up to 3 carbon atoms or phenoxy or benzyloxy radicals and wherein $R_1$, $R_2$, $R_3$, $R_4$ and $R_5$, can also represent hydrogen atoms and two adjacent symbols can together also represent a methylenedioxy radical and in which $R_6$ is a hydrogen atom or a straight or branch-chained alkyl or alkenyl radical containing up to 3 carbon atoms, a cyclopropylmethyl, cyclobutylmethyl, cyclopentylmethyl or cyclohexylmethyl radical, an alkoxycarbonyl radical containing 2 to 4 carbon atoms, a benzyl or phenethyl radical, trifluoroacetyl or an acyl radical derived from a monobasic aliphatic acid containing up to 5 carbon atoms or from a phenylalkane acid containing 8 to 11 carbon atoms.

Another preferred group of compounds according to the present invention are those wherein $R_1$ and $R_3$, which can be the same or different, are hydrogen atoms, hydroxyl groups or methoxy radicals, $R_2$ is a methoxy radical, $R_4$ and $R_5$, which can be the same or different, are hydroxyl groups or methoxy radicals or $R_4$ and $R_5$ together represent a methylenedioxy radical and $R_6$ is a hydrogen atom or a methyl or trifluoroacetyl radical.

The process according to the present invention is especially suitable for compounds in which $R_1$ to $R_5$ represent hydroxyl, methoxy, ethoxy, phenoxy or benzyloxy radicals or in which two adjacent radicals together represent a methylenedioxy radical but in which at least one of the symbols $R_1$ and $R_3$ must be a hydroxyl group and $R_6$ is preferably a hydrogen atom, or a methyl, ethyl, propyl, allyl, dimethylallyl, methallyl, benzyl, phenylethyl, formyl, acetyl, trifluoroacetyl, benzoyl, methoxy or ethoxycarbonyl radical.

The compounds according to the present invention of general formula (I), wherein the cyclic nitrogen atom is not substituted (i.e. is an NH) can be N-substituted in situ or subsequently by known methods. Thus, for example, by reaction with a reactive alkyl derivative, for example allyl bromide, the nitrogen can be alkylated. By reaction with a reactive acyl derivative, there are obtained the N-acyl derivatives which, if desired, can be converted by reduction into substituted amines, for example with lithium aluminum hydride.

An especially advantageous variant for the preparation of the N-nor compounds of general formula (I) ($R_6$=H) is that, for the cyclisation, use is made of hydroxy-4-benzyltetrahydroisoquinolines of general formula (II), the nitrogen atom of which carries a suitable protective group which can easily be split off after the reaction has taken place. Preferred protective groups include the trifluoroacetyl and benzyl radicals.

The phenolic dibenz(de,g)isoquinolines according to the present invention can, if desired, be O-substituted and preferably O-methylated in known manner. Examples of methylating agents which can be used include diazomethane, methyl iodide and dimethyl sulphate, which are reacted under known conditions. An especially preferred embodiment is methylation with phenyltrimethylammonium hydroxide in the manner described in Federal Republic of Germany Patent Specification No. 2,757,335.

Pharmacology

In animal experiments, the compounds according to the present invention have a low toxicity and a dosage-dependent, preponderantly neuroleptic action on the central nervous system.

1. Acute toxicity

The $LD_{50}$ in male mice is from 600 to 1200 mg./kg., in the case of intragastral administration:

| Example No. | $LD_{50}$ value in mg./kg. |
|---|---|
| 8 | 800 |
| 9 | about 1200 |
| 10 | about 1200 |
| 7 | about 600 |

2. Behavioural test in rats, modified after Irwin, Psychopharmacologica. (Berl.); 13, pgs. 222–257 (1968).

| Example No. | | behaviour at: |
|---|---|---|
| 8 | 300 mg./kg.: | sedation, reduced muscle tonus, ptosis, catatonia and lowering of the body temperature |
| 9 | 150 mg./kg.: | sedation, catatonia, lowering of the body temperature |
|   | 300 mg./kg.: | strengthening of the symptoms |
| 10 | 150 mg./kg.: | sedation, reduced muscle tonus, catatonia, lowering of the body temperature |
| 7 | 150 mg./kg.: | sedation, ptosis, catatonia, lowering of the body temperature |

3. Prolongation of evipan sodium narcosis, Arch. Int. Pharmacodyn; 126, pgs. 219–227 (1960).

| Example No. | dosage mg./kg. | prolongation of the sleeping time in % |
|---|---|---|
| 8 | 50 | 64 |
| 9 | 50 | 339 |
|   | 100 | 417 |
| 10 | 50 | 268 |
|   | 100 | 347 |
| 7 | 50 | 147 |
|   | 100 | 324 |

4. Alphalysis, Medizinische Wochenschrift; 81, pg. 352 (1951).

The alphalytic activity of the compounds of Examples 8 and 9 was tested on dogs. In the case of both compounds, from 1 mg./kg. i.v., a distinct alphalytic activity is detectable. In the case of the compound of Example 8, the action could also be confirmed after intraduodenal administration.

The compounds of general formula (I) according to the present invention can be administered orally or parenterally in liquid or solid form. As injection solution, water is preferably used which contains the additives usual in the case of injection solutions, for example stabilising agents, solubilising agents and buffers. Additives of this kind include, for example, tartrate and citrate buffers, ethanol, complex formers (such as ethylenediamine-tetraacetic acid and its nontoxic salts) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatin, agar-agar, calcium phosphate, magnesium stearate, animal and vegetable fats and solid high molecular weight polymers (such as polyethylene glycol). Compositions suitable for oral administration can, if desired, contain additional flavouring and/or sweetening materials.

The enterally administered individual doses are in the range of from about 2 to 200 mg., whereas parenterally about 1 to 50 mg. are given. For oral administration to a 70 kg. mammal, the preferred dose range is from 50–200 mg.

The following Examples are given for the purpose of illustrating the present invention:

EXAMPLE 1

(±)-5,6,6a,7-Tetrahydro-3-hydroxy-2-methoxy-9,10-methylenedioxy-5-methyl-4H-dibenz(de,g)isoquinoline 8.2 g. (25.05 mMol) (±)-8-Hydroxy-7-methoxy-2-methyl-4-(3,4-methylenedioxybenzyl)-1,2,3,4-tetrahydroisoquinoline are dissolved in a mixture of 80 ml. anhydrous methylene chloride and 80 ml. trifluoroacetic acid and mixed at $-10°$ C., with the exclusion of moisture and in an inert gas atmosphere, with a solution of 2.46 ml. (4.53 g., 26.12 mMol) vanadium oxytrichloride in 80 ml. anhydrous methylene chloride with stirring and in the course of 10 minutes. The reaction instantaneously becomes dark blue coloured, with the formation of a precipitate. At the end of the addition, stirring is continued for 10 minutes at $-10°$ C. and thereafter for 30 minutes at 0° C., thereafter the reaction mixture is again cooled to $-10°$ C. and, for completing the reaction, a solution of 0.9 ml. (1.66 g., 9.56 mMol) vanadium oxytrichloride in 16 ml. anhydrous methylene chloride is added thereto dropwise. Thereafter, the reaction mixture is stirred for 30 minutes at 0° C. For working up, the reaction is concentrated at a water-pump vacuum to about one third of its volume and then poured into ice water. Upon mixing with chloroform, the product starts to crystallise out in the form of its trifluoroacetate. 8.1 g. (±)-5,6,6a7-Tetrahydro-3-hydroxy-2-methoxy-9,10-methylenedioxy-5-methyl-4H-dibenz(de,g)isoquinoline trifluoroacetate are obtained. After working up the chloroform extract and crystallising the residue from chloroform, there are obtained a further 2.55 g. of the product as the trifluoroacetate. The total yield is thus 10.65 g. (96.8% of theory); m.p. 227°–237° C.

EXAMPLE 2

(±)-5,6,6a,7-Tetrahydro-3-hydroxy-2,9,10-trimethoxy-5-methyl-4H-dibenz(de,g)isoquinoline 1 g. (2.91 mMol) (±)-8-Hydroxy-7-methoxy-4-(3,4-dimethoxybenzyl)-2-methyl-1,2,3,4-tetrahydroisoquinoline is dissolved, with cooling, in a mixture of 10 ml. trifluoroacetic acid and 10 ml. anhydrous methylene chloride. A solution of 0.3 ml. (0.55 g., 3.19 mMol) vanadium oxytrichloride in 10 ml. anhydrous methylene chloride is added dropwise to this solution, with stirring, at $-10°$ C. in an inert gas atmosphere. The deep blue reaction mixture is stirred for 10 minutes at $-10°$ C. and for 30 minutes at 0° C., thereafter, at $-10°$ C., a further 0.11 ml. (0.2 g., 1.17 mMol) vanadium oxytrichloride in 2 ml. anhydrous methylene chloride is added thereto. The reaction mixture is allowed to warm up to ambient temperature, evaporated in a vacuum to one third of its volume and the concentrate partitioned between ice water and chloroform. The usual work up and crystallisation from chloroform/diethyl ether gives 752 mg. (±)-5,6,6a,7-tetrahydro-3-hydroxy-2,9,10-trimethoxy-5-methyl-4H-dibenz(de,g)isoquinoline in the form of its trifluoroacetate. The yield is 56.7% of theory. The free base (m.p. 195°–206° C.) is obtained from this salt by treatment with ammonia.

EXAMPLE 3

(±)-5,6,6a,7-Tetrahydro-1-hydroxy-2,9,10-trimethoxy-5-methyl-4H-dibenz(de,g)isoquinoline 10 g. (29.12 mMol) (±)-6-Hydroxy-4-(3,4-dimethoxybenzyl)-7-methoxy-2-methyl-1,2,3,4-tetrahydroisoquinoline are dissolved at 0° C. in trifluoroacetic acid, with the exclusion of moisture. The solution is cooled in an inert gas atmosphere to $-10°$ C. and, while stirring, a solution of 6 ml. (11.04 g., 63.7 mMol) vanadium oxytrichloride in 60 ml. anhydrous methylene chloride is added dropwise in the course of 10 minutes. When the addition is completed, the reaction mixture is further stirred for 10 minutes at $-10°$ C. The TLC analysis (silica gel, chloroform/methanol 9:1 v/v) shows that almost all the starting material has reacted and the reaction product consists essentially of one main spot. The reaction mixture is evaporated at ambient temperature in a vacuum and the residue is mixed with ice water and then exhaustively extracted with chloroform. After working up and crystallising (chloroform-diethyl ether), there are obtained 11.05 g. (83.3% of theory) (±)-5,6,6a,7-tetrahydro-1-hydroxy-2,9,10-trimethoxy-5-methyl-4H-dibenz(de,g)isoquinoline in the form of the crystalline trifluoroacetate as a crude product; m.p. 196°–210° C.

EXAMPLE 4

(±)-5-Trifluoroacetyl-5,6,6a,7-tetrahydro-1-hydroxy-2,9,10-trimethoxy-4H-dibenz(de,g)isoquinoline 15.7 g. (36.9 mMol) (±)-N-Trifluoroacetyl-6-hydroxy-7-methoxy-4-(3,4-dimethoxybenzyl)-1,2,3,4-tetrahydroisoquinoline are dissolved in 145 ml. dry methylene chloride and mixed with 145 ml. trifluoroacetic acid, while cooling with ice water and with the exclusion of moisture. A solution of 2.8 ml. (5.15 g., 29.73 mMol) vanadium oxytrichloride in 65 ml. anhydrous methylene chloride are added dropwise in the course of 10 minutes to this solution at $-10°$ C., while stirring and in an inert gas atmosphere. After 30 minutes, a further addition of 2.8 ml. vanadium oxytrichloride in 65 ml. anhydrous methylene chloride takes place. The dark coloured reaction mixture is stirred for a further 10 minutes at −10° C. The TLC analysis (silica gel, chloroform/methanol 9:1 v/v) shows that the starting material is completely gone. The reaction mixture is concentrated in a vacuum in a rotary evaporator at ambient temperature to about one third of its original volume and the residue than partitioned between water and methylene chloride. After working up the extracts and crystallising the crude product from acetone, there is obtained (±)-5-trifluoroacetyl-5,6,6a,7-tetrahydro-1-hydroxy-2,9,10-trimethoxy-4H-dibenz(de,g)isoquinoline in practically quantitative yield; m.p. 210°–217° C.

The (±)-N-Trifluoroacetyl-6-hydroxy-7-methoxy-4-(3,4-dimethoxybenzyl)-1,2,3,4-tetrahydroisoquinoline used as starting material is prepared as follows:

10 g. 6-Hydroxy-7-methoxy-4-(3,4-dimethoxybenzyl)isoquinoline (see Tetrahedron, 35, 2555–2559/1979) are mixed with a mixture of 100 ml. concentrated hydrochloric acid and 750 ml. water. The mixture is heated to reflux temperature and 30.4 g. zinc dust added portionwise to the clear solution. The reaction mixture is kept at reflux temperature for 20 hours, while stirring. Thereafter, a further 100 ml. concentrated hydrochloric acid are added thereto and again the same amount of zinc dust. After boiling under reflux for 20 hours, the same procedure is, if necessary, repeated (TLC monitoring for starting material). The zinc salts are filtered off and then washed with water. The filtrate is rendered basic with concentrated ammonia solution, while cooling with ice, and extracted with methylene chloride. A part of the reaction product thereby precipitates out in crystalline form and is combined with the solid material obtained by evaporation of the methylene chloride extract. The yield is about 100% of theory.

21.15 g. of the so obtained (±)-6-hydroxy-7-methoxy-4-(3,4-dimethoxybenzyl)-1,2,3,4-tetrahydroisoquinoline are taken up in 200 ml. pyridine and mixed dropwise with 36.5 ml. trifluoroacetic anhydride at 0° C., with the exclusion of moisture. The reaction mixture is allowed to react for 1 hour at 0° C. and for 1 hour at ambient temperature. Thereafter, it is poured into ice water and extracted with methylene chloride. The combined methylene chloride extracts are successively washed with 2 N hydrochloric acid and with water. After evaporating off the solvent in a vacuum, the residue is taken up in 300 ml. methanol and added to a suspension of 32 g. sodium bicarbonate in 156 ml. water. The reaction mixture is stirred for 1 hour at ambient temperature and then partitioned between water and methylene chloride. Usual working up gives 25.55 g. (93.6% of theory) (±)-N-trifluoroacetyl-6-hydroxy-7-methoxy-4-(3,4-dimethoxybenzyl)-1,2,3,4-tetrahydroisoquinoline in the form of a brown, TLC-homogeneous syrup which can be used for the cyclisation reaction without further purification.

EXAMPLE 5

(±)-5,6,6a,7-Tetrahydro-1,9-dihydroxy-2,10-dimethoxy-5-methyl-4H-dibenz(de,g)isoquinoline 1 g. (3 mMol) (±)-6-Hydroxy-7-methoxy-4-(3-hydroxy-4-methoxybenzyl)-2-methyl-1,2,3,4-tetrahydroisoquinoline is dissolved, with ice cooling, in 25 ml. trifluoroacetic acid and mixed at −10° C. with a solution of 0.42 ml. (0.77 g., 4.5 mMol) vanadium oxytrichloride in 5 ml. anhydrous methylene chloride within the course of 1 minute. The reaction mixture is allowed to react for 3 hours at −10° C., then concentrated in a vacuum to about one third of its volume and the concentrate partitioned between methylene chloride and water. Usual work up and crystallisation from acetone/diethyl ether gives (±)-5,6,6a,7-Tetrahydro-1,9-dihydroxy-2,10-dimethoxy-5-methyl-4H-dibenz(de,g)isoquinoline in the form of its trifluoroacetate; m.p. 208°–215° C.; yield 60–70% of theory. Hydrochloride: m.p. >300° C. (decomp.), after recrystallisation from methanol/chloroform.

EXAMPLE 6

(±)-5,6,6a,7-Tetrahydro-3,9-dihydroxy-2,10-dimethoxy-5-methyl-4H-dibenz(de,g)isoquinoline 1 g. (3 mMol) (±)-8-Hydroxy-7-methoxy-4-(3-hydroxy-4-methoxybenzyl)-2-methyl-1,2,3,4-tetrahydroisoquinoline (m.p. 175°–187° C.) is dissolved, while cooling, in 25 ml. trifluoroacetic acid and mixed at −10° C., in an inert gas atmosphere, with a solution of 0.42 ml. (0.77 g., 4.5 mMol) vanadium oxytrichloride in 15 ml. anhydrous methylene chloride. After 10 minutes, the reaction mixture is concentrated in a vacuum at ambient temperature to about one third of its volume and partitioned between ice water and methylene chloride. After work up and crystallising from chloroform, there is obtained 1.1 g. (83% of theory) (±)-5,6,6a,7-tetrahydro-3,9-dihydroxy-2,10-dimethoxy-5-methyl-4H-dibenz(de,g)isoquinoline in the form of its trifluoroacetate; m.p. 300° C.

The free base (m.p. 114°–130° C.) is obtained from the trifluoroacetate by treatment wih ammonia and crystallisation from methanol.

EXAMPLE 7

(±)-5,6,6a,7-Tetrahydro-1,2,9,10-tetramethoxy-4H-dibenz(de,g)isoquinoline 9.7 g. (±)-5-Trifluoroacetyl-5,6,6a,7-tetrahydro-1-hydroxy-2,9,10-trimethoxy-4-dibenz(de,g)isoquinoline (see Example 4) are dissolved in 300 ml. of a mixture of toluene and dimethyl formamide (9:1 v/v) and heated to 100° C. To this are added dropwise, within the course of about 10 minutes, 15 ml. of a 1 N solution of phenyl-trimethylammonium hydroxide in methanol, with vigorous stirring and the simultaneous distilling off of an azeotropic mixture of methanol and toluene. When the addition is finished, the reaction mixture is heated until the temperature of distillate passing over is about 111° C. Heating under reflux is then continued for a further hour. If, according to the TLC analysis, starting material is still present, a further portion of the methylation solution is added thereto and the above-described procedure repeated. For the isolation of the product, the reaction mixture is filtered and the filtrate is evaporated in a vacuum. After partitioning the residue between water and methylene chloride and the usual working up, (±)-N-trifluoroacetyl-5,6,6a,7-tetrahydro-1,2,9,10-tetramethoxy-4H-dibenz(de,g)isoquinoline is obtained in the form of an oily crude product which, without further purification, is taken up in 226 ml. of a 1 N solution of potassium hydroxide in methanol and mixed portionwise at about 5° C. within the course of 2 hours with 2.8 g. sodium borohydride. The reaction mixture is stirred overnight at ambient temperature, then mixed with 100 ml. acetone, evaporated in a vacuum and the residue partitioned between water and methylene chloride. After work up and chromatography on silica gel with chloroform as eluent, there is obtained (±)-5,6,6a,7-tetrahydro-1,2,9,10-tetramethoxy-4H-dibenz(de,g)isoquinoline, which is crystallised from ethanolic hydrochloric acid in the form of its hydrochloride; m.p. 245°–249° C.

EXAMPLE 8

(±)-5,6,6a,7-Tetrahydro-1,2,9,10-tetramethoxy-5-methyl-4H-dibenz(de,g)isoquinoline 2.2 g. (±)-5,6,6a,7-Tetrahydro-1-hydroxy-2,9,10-trimethoxy-5-methyl-4H-dibenz(de,g)isoquinoline trifluoro acetate (see Example 3) are dissolved in 10 ml. of a mixture of toluene and dimethylformamide (9:1 v/v) and methylated with phenyltrimethylammonium hydroxide in a manner analogous to that described in Example 7. When the reaction is finished, the reaction mixture is evaporated in a vacuum and the residue is partitioned between water and methylene chloride. The organic phase is worked up in the usual manner and the crude product obtained is converted, either directly or after previous chromatography on silica gel with chloroform as eluent, into the hydrochloride by treatment with ethanolic hydrochloric acid. Crystallisation from ethanol/diethyl ether gives (±)-5,6,6a,7-tetrahydro-1,2,9,10-tetramethoxy-5-methyl-4H-dibenz(de,g)isoquinoline in the form of a yellow hydrochloride; m.p. 212°–225° C.

EXAMPLE 9

(±)-5,6,6a,7-tetrahydro-2,3-dimethoxy-9,10-methylenedioxy-5-methyl-4H-dibenz(de,g)isoquinoline 10.65 g. (±)-5,6,6a,7-tetrahydro-3-hydroxy-2-methoxy-9,10-methylenedioxy-5-methyl-4H-dibenz(de,g)isoquinoline trifluoroacetate (see Example 1) are dissolved in 500 ml. of a mixture of toluene and dimethyl formamide (9:1) in a manner analogous to that described in Example 7 and methylated with phenyltrimethyl ammonium hydroxide. When the methylation is finished (monitoring with TLC), the reaction mixture is evaporated in a vacuum. After partitioning the residue between water and methylene chloride, working up the organic phase and crystallising from methanol/chloroform, there is obtained (±)-5,6,6a,7-tetrahydro-2,3-dimethoxy-9,10-methylenedioxy-5-methyl-4H-dibenz(de,g)isoquinoline in the form of cream-coloured crystals; m.p. 169°–172° C.

EXAMPLE 10

(±)-5,6,6a,7-Tetrahydro-2,3,9,10-tetramethoxy-5-methyl-4H-dibenz(de,g)isoquinoline 9.1 g. (±)-5,6,6a,7-Tetrahydro-3-hydroxy-2,9,10-trimethoxy-5-methyl-4H-dibenz(de,g)isoquinoline (see Example 2) are reacted with phenyltrimethylammonium hydroxide in toluene/dimethylformamide in a manner analogous to that described in Example 7. When the methylation is finished, the reaction mixture is worked up in the manner described in Example 7. By chromatography of the crude product on silica gel (elution with chloroform +1% triethylamine) and crystallisation from chloroform-diethyl ether, there is obtained (±)-5,6,6a,7-tetrahydro-2,3,9,10-tetramethoxy-5-methyl-4H-dibenz(de,g)isoquinoline in the form of beige crystals; m.p. 170°–177° C.

We claim:
1. A compound having the structural formula

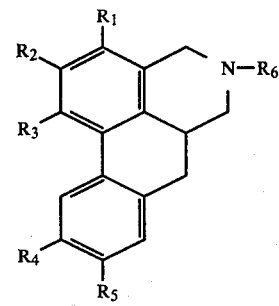

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is hydrogen, straight or branched-chain alkyl of from 1 to 5 carbon atoms, straight or branched-chain alkenyl of from 2 to 5 carbon atoms, cycloalkylalkyl of from 4 to 7 carbon atoms, alkoxy carbonyl of from 2 to 6 carbon atoms, aralkyl of from 7 to 11 carbon atoms, or acyl which is derived from an aliphatic, araliphatic or aromatic carboxylic acid of from 1 to 11 carbon atoms; and the pharmaceutically acceptable salts thereof; excluding 5,6,6a,7-tetrahydro-1-hydroxy-2,9,10-trimethoxy-5-methyl-4H-dibenz(de,g)isoquinoline and 5,6,6a,7-tetrahydro-1,2,9,10-tetramethoxy-5-methyl-4H-dibenz(de,g)isoquinoline.

2. The compounds defined in claim 1 wherein $R_1$, $R_2$, $R_3$, $R_4$, and $R_5$ may be the same or different and are hydroxy, straight or branched-chain alkoxy groups of from 1 to 3 carbon atoms, phenoxy, benzyloxy, two adjacent groups may be methylenedioxy or hydrogen provided $R_4$ and $R_5$ are not simultaneously hydrogen; $R_6$ is hydrogen, straight or branched-chain alkyl of from 1 to 3 carbon atoms, straight or branched-chain alkenyl of from 2 to 4 carbon atoms, cyclopropylmethyl, cyclobutylmethyl, cyclopentylmethyl, cyclohexylmethyl, alkoxycarbonyl of from 2 to 4 carbon atoms, benzyl, phenethyl, aliphatic acyl of from 1 to 5 carbon atoms, phenyl aliphatic acyl of from 8 to 11 carbon atoms; and the pharmaceutically acceptable salts thereof; excluding 5,6,6a,7-tetrahydro-1-hydroxy-2,9,10-trimethoxy-5-methyl-4H-dibenz(de,g)-isoquinoline and 5,6,6a,7-tetrahydro-1,2,9,10-tetra-methoxy-5-methyl-4H-dibenz(de,g)isoquinoline.

3. The compounds defined in claim 1 wherein $R_1$ and $R_3$ may be the same or different and are hydrogen, hydroxy or methoxy; $R_2$ is methoxy, $R_4$ and $R_5$ may be the same or different and are hydroxy, methoxy or together form a methylenedioxy group, $R_6$ is hydrogen, methyl, or trifluoroacetyl; and the pharmaceutically acceptable salts thereof; excluding 5,6,6a,7-tetrahydro-1-hydroxy-2,9,10-trimethoxy-5-methyl-4H-dibenz(de,g)isoquinoline and 5,6,6a,7-tetrahydro-1,2,9,10-tetramethoxy-5-methyl-4H-dibenz(de,g)isoquinoline.

4. The compound (±)-5,6,6a,7-Tetrahydro-3-hydroxy-2-methoxy-9,10-methylenedioxy-5-methyl-4H-dibenz(de,g)isoquinoline and the pharmaceutically acceptable salts thereof.

5. The compound (±)-5,6,6a,7-Tetrahydro-3-hydroxy-2,9,10-trimethoxy-5-methyl-4H-dibenz(de,g)isoquinoline and the pharmaceutically acceptable salts thereof.

6. The compound (±)-5-Trifluoroacetyl-5,6,6a,7-tetrahydro-1-hydroxy-2,9,10-trimethoxy-4H-dibenz(de,g)isoquinoline and the pharmaceutically acceptable salts thereof.

7. The compound (±)-5,6,6a,7-Tetrahydro-1,9-dihydroxy-2,10-dimethoxy-5-methyl-4H-dibenz(de,g)isoquinoline and the pharmaceutically acceptable salts thereof.

8. The compound (±)-5,6,6a,7-Tetrahydro-3,9-dihydroxy-2,10-dimethoxy-5-methyl-4H-dibenz(de,g)isoquinoline and the pharmaceutically acceptable salts thereof.

9. The compound (±)-5,6,6a,7-Tetrahydro-1,2,9,10-tetramethoxy-4H-dibenz(de,g)isoquinoline and the pharmaceutically acceptable salts thereof.

10. The compound (±)-5,6,6a,7-Tetrahydro-2,3-dimethoxy-9,10-methylenedioxy-5-methyl-4H-dibenz(de,g)isoquinoline and the pharmaceutically acceptable salts thereof.

11. The compound (±)-5,6,6a,7-Tetrahydro-2,3,9,10-tetramethoxy-5-methyl-4H-dibenz(de,g)isoquinoline and the pharmaceutically acceptable salts thereof.

12. A compound having the structural formula

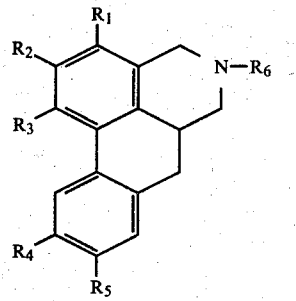

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is trifluoroacetyl and the pharmaceutically acceptable salts thereof.

13. A pharmaceutical composition useful for treating diseases of the central nervous system in a mammal consisting essentially of a compound having the structural formula:

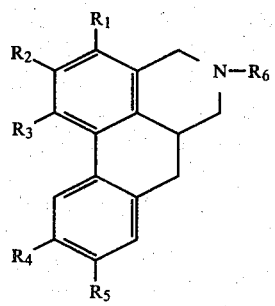

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is hydrogen, straight or branched-chain alkyl of from 1 to 5 carbon atoms, straight or branched-chain alkenyl of from 2 to 5 carbon atoms, cycloalkylalkyl of from 4 to 7 carbon atoms, alkoxy carbonyl of from 2 to 6 carbon atoms, aralkyl of from 7 to 11 carbon atoms, or acyl which is derived from an aliphatic, araliphatic or aromatic carboxylic acid of from 1 to 11 carbon atoms; and the pharmaceutically acceptable salts thereof; excluding 5,6,6a,7-tetrahydro-1-hydroxy-2,9,10-trimethoxy-5-methyl-4H-dibenz(de,g)isoquinoline and 5,6,6a,7-tetrahydro-1,2,9,10-tetramethoxy-5-methyl-4H-dibenz(de,g)isoquinoline or mixtures thereof in an effective amount for treating said diseases in combination with a pharmaceutically acceptable carrier.

14. A pharmaceutical composition according to claim 13 wherein $R_6$ is trifluoroacetyl.

15. A method for treating diseases of the central nervous system in a mammal in need of such treatment; which comprises administering an effective amount for treating said diseases of a pharmaceutical composition consisting essentially of a compound of the structural formula:

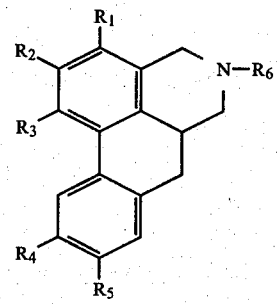

wherein $R_1$, $R_2$, $R_3$, $R_4$ and $R_5$ may be the same or different and are hydroxy, straight or branched-chain alkoxy of from 1 to 5 carbon atoms, phenoxy, benzyloxy, two adjacent groups may be methylenedioxy, or hydrogen provided $R_4$ and $R_5$ are not simultaneously hydrogen; $R_6$ is hydrogen, straight or branched chain alkyl of from 1 to 5 carbon atoms, straight or branched chain alkenyl of from 2 to 5 carbon atoms, cycloalkylalkyl of from 4 to 7 carbon atoms, alkoxy carbonyl of from 2 to 6 carbon atoms, aralkyl of from 7 to 11 carbon atoms, or acyl which is derived from an aliphatic, araliphatic or aromatic carboxylic acid of from 1 to 11 carbon atoms; and the pharmaceutically acceptable salts thereof; excluding 5,6,6a,7-tetrahydro-1-hydroxy-2,9,10-trimethoxy-5-methyl-4H-dibenz(de,g)isoquinoline and 5,6,6a,7-tetrahydro-1,2,9,10-tetramethoxy-5-methyl-4H-dibenz(de,g)isoquinoline to said mammal.

16. A method according to claim 15 wherein $R_6$ is trifluoroacetyl.

17. The method of claim 15 and 16 wherein said effective amount is in individual doses of 2 to about 200 mg. per 70 kg. mammal administered internally.

18. The method of claim 15 and 16 wherein said effective amount is in individual doses of about 1 to 50 mg. per 70 kg. mammal administered parenterally.

19. The method of claim 15 and 16 wherein said effective amount is in individual doses of 50 to 200 mg. per 70 kg. mammal administered orally.

* * * * *